United States Patent
Cui

(10) Patent No.: US 12,311,078 B2
(45) Date of Patent: May 27, 2025

(54) METHODS AND COMPOSITIONS FOR CELL TRANSPLANTATION

(71) Applicant: Georgetown University, Washington, DC (US)

(72) Inventor: Wanxing Cui, Derwood, MD (US)

(73) Assignee: Georgetown University, Washington, DC (US)

( * ) Notice: Subject to any disclaimer, the term of this patent is extended or adjusted under 35 U.S.C. 154(b) by 1111 days.

(21) Appl. No.: 17/265,196

(22) PCT Filed: Aug. 2, 2019

(86) PCT No.: PCT/US2019/045017
§ 371 (c)(1),
(2) Date: Feb. 1, 2021

(87) PCT Pub. No.: WO2020/028885
PCT Pub. Date: Feb. 6, 2020

(65) Prior Publication Data
US 2021/0220519 A1   Jul. 22, 2021

Related U.S. Application Data

(60) Provisional application No. 62/713,732, filed on Aug. 2, 2018.

(51) Int. Cl.
*A61L 27/36* (2006.01)
*A61K 35/39* (2015.01)
*A61L 27/38* (2006.01)

(52) U.S. Cl.
CPC .......... *A61L 27/3683* (2013.01); *A61K 35/39* (2013.01); *A61L 27/3604* (2013.01); *A61L 27/3804* (2013.01)

(58) Field of Classification Search
CPC ............. A61L 27/3683; A61L 27/3604; A61L 27/3804; A61K 35/39
See application file for complete search history.

(56) References Cited

U.S. PATENT DOCUMENTS

2011/0027250 A1   2/2011   Messersmith et al.
2011/0287071 A1   11/2011  Mitrani
2012/0245705 A1   9/2012   Hasilo et al.

OTHER PUBLICATIONS

Desai, T., and Shea, L. D., "Advances in islet encapsulation technologies," Nat Rev Drug Discov 16(5):338-350. doi: 10.1038/nrd.2016.232. (Year: 2016).*
Navaei-Nigjeh, M., et al., "Reduction of marginal mass required for successful islet transplantation in a diabetic rat model using adipose tissue-derived mesenchymal stromal cells," Cytotherapy 20(9): 1124-1142. doi: 10.1016/j.jcyt.2018.06.001. Epub Jul. 29, 2018. (Year: 2018).*
Sionov, R. V., et al., "Beta Cells Secrete Significant and Regulated Levels of Insulin for Long Periods when Seeded onto Acellular Micro-Scaffold," Tissue Eng Part A 21(21-22): 2691-2702. doi: 10.1089/ten.TEA.2014.0711. (Year: 2015).*
Wilshaw, S. P., et al., "Biocompatibility and potential of acellular human amniotic membrane to support the attachment and proliferation of allogeneic cells," Tissue Eng Part A 14(4): 463-472. doi: 10.1089/tea.2007.0145. (Year: 2008).*
Toda, A., et al., "The potential of amniotic membrane/amnion-derived cells for regeneration of various tissues," J Pharmacol Sci 105 (3): 215-228. doi: 10.1254/jphs.cr0070034. (Year: 2007).*
Bromberg, J. S., "Islet implantation in a pocket," Nat Biotechnol 33(5):493-494. doi: 10.1038/nbt.3216. (Year: 2015).*
Brubaker, C. E., "Biological performance of mussel-inspired adhesive in extrahepatic islet transplantation," et al., Biomaterials 31(3): 420-427. doi: 10.1016/j.biomaterials.2009.09.062. (Year: 2009).*

* cited by examiner

*Primary Examiner* — Tracy Vivlemore
*Assistant Examiner* — Eric J Rogers
(74) *Attorney, Agent, or Firm* — Grimes & Yvon LLP

(57) ABSTRACT

Methods of transplanting target cells into a subject in need thereof. The methods generally comprise creating a sealed transplantation space by attaching an acellular membrane to the surface of a visceral organ or tissue in the subject in a manner such that a sealed space is created between the surface of the visceral organ or tissue and the membrane, and inserting a mixture of support cells and the target cells into the sealed transplantation space.

14 Claims, 3 Drawing Sheets

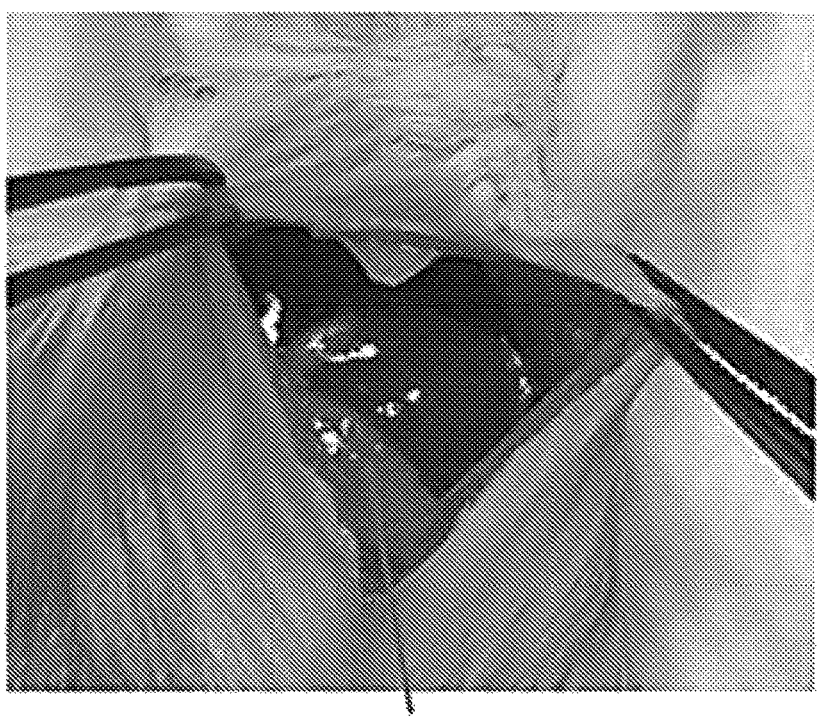
Figure 2A
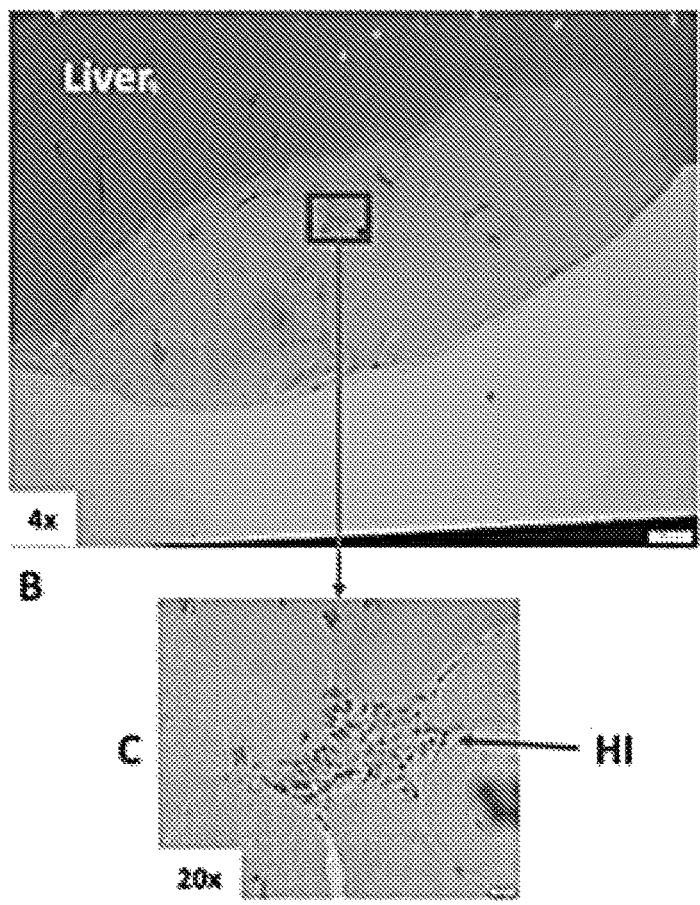
Figure 2B
Figure 2C

METHODS AND COMPOSITIONS FOR CELL TRANSPLANTATION

CROSS-REFERENCE TO RELATED APPLICATIONS

This application is a National Stage of International Application No. PCT/US2019/045017 filed on Aug. 2, 2019, which claims the benefit of priority to U.S. Provisional Application No. 62/713,732 filed on Aug. 2, 2018, each of which is herein incorporated by reference in its entirety for all purposes.

FIELD OF THE INVENTION

The present invention relates to compositions and methods for transplanting target cells into a subject in need thereof. The methods generally comprise creating a sealed transplantation space by attaching an acellular membrane to the surface of a visceral organ or tissue in the subject in a manner such that a sealed space is created between the surface of the visceral organ or tissue and the membrane, and inserting a mixture of support cells and the target cells into the sealed transplantation space.

BACKGROUND OF THE INVENTION

Existing technologies for engraftment of cells are focused on, for example, insulin-producing cell induction with human amniotic epithelial cells (hAECs) or simply biobarrier applications using only an untreated amniotic membrane. Using the current standard procedures, when islets are infused through the portal vein for islet transplantation, more than 50% of the human islet graft is lost within 3 days due, at least in part, to an instant blood-mediated inflammation reaction (IBMIR). Placing the islets outside of the blood stream may avoid islet cell loss from IBMIR. There is, however, no ideal transplantation site for islet cell grafting despite efforts to aggressively seek alternative sites such as bone marrow, the omentum, the submucosal layer of stomach, and/or subcutaneous sites.

The liver has been the site of choice for islet transplantation in clinical practice. In recent years, it has become increasingly recognized that intra-portal infusion of isolated islet cells may not provide the ideal microenvironment for islets due to various factors that contribute to the loss of islet mass early after infusion. The crucial events occurring in the hours and days after islet infusion influence the success of transplantation. Most notably, during islet infusion, an IBMIR is elicited when islets are exposed to blood, involving the coagulation cascade that includes complement activation. These inflammatory processes are triggered by tissue factors secreted by endocrine cells, which leads to the generation of thrombin. Thrombin-activated platelets bind to the islet surface, and then the amplification loop involving factor XI and activated platelets generate a fibrin capsule surrounding the islets. Intra-portal islet infusion is also associated with thrombosis and hepatic tissue ischemia caused by islet entrapment in liver sinusoids that leads to sinusoidal endothelial cell activation and functional impairment. Finally, IBMIR culminates in the disruption of islet morphology by infiltrating leukocytes. Polymorphonuclear cells (PMNs) are the predominant cell type infiltrating the islets, attracted by the upregulation and release of ischemia-induced molecules, i.e., tissue factor, IL-1 beta, tumor necrosis factor-alpha (TNF-alpha), nitric oxide, high-mobility group box 1 (HMGB1); and by proinflammatory signals, i.e., monocyte chemoattractant protein (MCP-1), IL-8, IL-6, released from the islet. After activation, PMNs secrete reactive oxygen species, leading to rapid and direct damage of the islets.

The current solutions to poor engraftment include application of anti-inflammation agents and/or anti-apoptosis agents through biological and/or bioengineering approaches. In the biological approach, the solution relies on the use of anti-inflammatory/anticoagulation agents or increasing the number of islets being engrafted.

There is a need to increase efficiency of cell transplantation to restore or increase normal function, such as glucose tolerance through insulin production.

SUMMARY OF THE INVENTION

The present invention relates to methods of transplanting target cells into a subject in need thereof. The methods generally comprise creating a sealed transplantation space by attaching an acellular membrane to the surface of a visceral organ or tissue in the subject such that a sealed space is created between the surface of the visceral organ or tissue and the membrane, and inserting a mixture of support cells and the target cells into the sealed transplantation space.

The present invention also relates to compositions comprising the outer surface of an intact visceral organ, an acellular membrane and a mixture of a population of at least one type of support cell and at least one type of target cell. The composition is configured to include a sealed space formed between the acellular membrane and the outer surface of the intact visceral organ, with the mixture of cells being disbursed in the sealed space.

BRIEF DESCRIPTION OF THE DRAWINGS

FIGS. 2A-2C show an image of the surgical procedure (FIG. 2A) and histological examination images at magnifications of 4× (FIG. 2B) and 20× (FIG. 2C), which confirm the presence of human islet (HI) cells at the site of grafting, 28 days after the initial procedure.

FIGS. 3A and 3C are images at 10× magnification, and FIGS. 3B and 3D at images at 20× magnification. HAM: decellularized human amniotic membrane; BV: Blood vessel; HAECs: human amniotic epithelial cells

DETAILED DESCRIPTION OF THE INVENTION

Figure 1A:
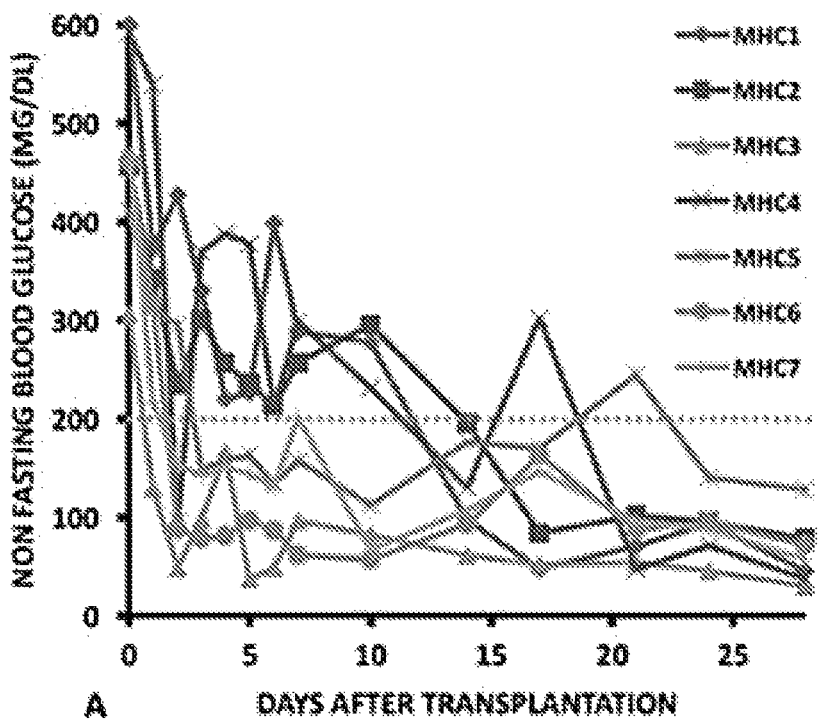
FIGS. 1A and 1B show non-fasting blood glucose levels (FIG. 1A) and body weight (FIG. 1B) in seven chemically-induced diabetic mice on which the methods of the present invention were performed.

The present invention relates to methods of transplanting target cells into a subject in need thereof. The methods generally comprise creating a sealed transplantation space by attaching an acellular membrane to the surface of a visceral organ or tissue in the subject in a manner such that a sealed space is created between the surface of the visceral organ or tissue and the membrane, and inserting a mixture of support cells and the target cells into the sealed transplantation space.

The terms "subject" and "patient" are used interchangeably herein. In some embodiments, the subject on which the methods of the present invention are performed is a mammal. In certain embodiments, the subject on which the methods of the present invention are performed is a dog, cat, mouse, rat, cow, horse, pig, or a human or non-human primate.

The methods described herein rely upon an acellular membrane. As used herein, the term "acellular membrane" is a tissue or portion thereof that has been subjected to decellularization processes such that the resident cells normally present in the tissue or portion thereof are removed, destroyed, and/or rendered metabolically inactive. The resulting tissue or portion thereof contains the extracellular matrix (ECM) in which little or no integrity or bioactivity is loss. Methods of decellularization of tissue are well-known in the art and the methods of the present invention are not necessarily dependent on a specific method of decellularizing the tissue or portion thereof. For example, methods of decellularization are disclosed in Crapo, P., et al., *Biomaterials*, 32(12):3233-3243 (2011), which is incorporated by reference herein in its entirety.

In one embodiment, the acellular membrane is a decellularized amniotic membrane. In another embodiment, the acellular membrane is decellularized bladder tissue. In another embodiment, the acellular membrane is decellularized small intestine tissue. In another embodiment, the acellular membrane is decellularized mesothelium. In another embodiment, the acellular membrane is decellularized pericardium.

The acellular membrane can be a xenograft, an allograft, or an autograft. These terms are well-known in the art. An autograft is a graft of tissue in which the same individual is both the donor and receiver of the tissue. In some embodiments comprising the use of an autograft for the acellular membrane, the subject may provide the tissue that is subjected to decellularization processes and subsequently receive the decellularized membrane upon performance of the methods of the present invention. The autograft acellular membrane may be stored for any period of time prior to the performance of the methods of the present invention. Alternatively, the autograft may be obtained from the donor and subjected to decellularization procedures to produce the acellular membrane, and the acellular membrane may then be attached to the recipient's organ or tissue, without the need for storing the acellular membrane for any length of time.

An allograft is a graft of tissue in which the donor and receiver of the tissue are from the same species, but not necessarily the same individual. In some embodiments comprising the use of an allograft for the acellular membrane, the donor may provide the tissue that is subjected to decellularization processes at any time prior to performance of the methods of the present invention. The allograft acellular membrane may be stored for any period of time prior to the performance of the methods of the present invention. Alternatively, the allograft may be obtained from the donor and subjected to decellularization procedures to produce the acellular membrane, and the acellular membrane may then be attached to the recipient's organ or tissue, without the need for storing the acellular membrane for any length of time.

A xenograft is a graft of tissue in which the donor and receiver of the tissue are not from the same species. In some embodiments comprising the use of a xenograft for the acellular membrane, the donor may provide the tissue that is subjected to decellularization processes at any time prior to performance of the methods of the present invention. The xenograft acellular membrane may be stored for any period of time prior to the performance of the methods of the present invention. Alternatively, the xenograft may be obtained from the donor and subjected to decellularization procedures to produce the acellular membrane, and the acellular membrane may then be attached to the recipient's organ or tissue, without the need for storing the acellular membrane for any length of time. In select embodiments comprising the use of a xenograft, the donor of the acellular membrane is a non-human mammal and the recipient (subject) of the acellular membrane is a human. In certain embodiments comprising the use of a xenograft, the donor of the acellular membrane is a pig or non-human primate and the recipient (subject) of the acellular membrane is a human.

In performing the methods of the present invention, the acellular membrane may be attached to the surface of a visceral organ or tissue. The acellular membrane may be attached to the organ or tissue by any means that creates a sealed space. In some embodiments, the acellular membrane may be attached to the surface of the visceral organ or tissue comprising placing the membrane on the organ or tissue surface and allowing the membrane and the organ or tissue surface to form a non-specific bond to create the seal. In some embodiments, the acellular membrane may be attached to the surface of the visceral organ or tissue comprising the use of tissue glue or adhesive by coating the outer rim of the membrane with the glue or adhesive and placing the coated membrane on the organ or tissue surface and allowing the membrane and the organ or tissue surface to bond to create a seal. In alternative embodiments, the acellular membrane may be placed on the organ or tissue surface and the glue or adhesive may be applied to the junction of the outer rim of the acellular membrane and the organ or tissue to allow the membrane and the organ or tissue surface to bond to create a seal. In some embodiments, the acellular membrane may be attached to the surface of the visceral organ or tissue comprising the use of stitching by stitching the outer rim of the membrane to the organ or tissue surface and allowing the membrane and the organ or tissue surface to bond to create a seal.

As used herein, the term visceral organ is used to mean an internal organ of the body that is generally contained within the chest or abdomen of the subject. Examples of visceral organs include, but are not limited to, heart, lungs, stomach, small intestine, large intestine, liver, pancreas, kidneys, thyroid gland, adrenal gland, gall bladder, spleen, bladder, ovaries, and uterus. Examples of visceral tissues that are not necessarily considered to be organs include, but are not limited to, large blood vessels such as but not limited to aorta; visceral muscle, such as but limited to diaphragm; peritoneum; pericardium; visceral fat pads; outer pleural membrane; and inner pleural membrane.

The acellular membrane is attached to the surface of the visceral organ or tissue in a manner described herein. As used here, the term "surface," when used in conjunction with a visceral organ or tissue is used to indicate the outer portion of the organ or tissue such that cutting the organ or tissue is generally not necessary for implantation of the acellular membrane. In general, the methods of the present invention may be performed by examining the visceral organ or tissue to locate a relatively flat surface or region of the organ or tissue such that the acellular membrane will not collapse or wrap around the surface of the organ or tissue. When the acellular membrane is placed on the outer surface of the organ or tissue in a manner that prevents the membrane from wrapping around or collapsing onto the surface of the organ, this can create a sealed space on the outer surface of the organ or tissue.

The sealed space that is created when performing the methods of the present invention need not be large, but the space must be able to accommodate insertions or injections of cells, generally dispersed within a liquid, into the space. The space must be sealed such that the cells, generally dispersed within a liquid, are contained within the space, or pouch. The sealed space, however, need not be air-tight or impervious to liquids, provided that the inserted cells remain within the space after initial insertion.

Once the sealed space is created, a mixture of cells may then be inserted into the space. The mixture of cells for the methods of the present invention may require at least two different populations of cells. One population of cells in the mixture may comprise a population of support cells. As used herein, the term "support cells" is used to mean a population of cells that have one or more properties that support the growth and/or increase in the number of target cells. The properties of the support cells include, but are not limited to, cells having at least one of innate anti-inflammatory or innate immunosuppressive properties. Other properties of the support cells include, but are not limited to, cells having at least one of angiogenic- or differentiation-promoting properties. As used herein the support properties of the support cells may be accomplished by any means, such as the cells produce and secrete anti-inflammatory factors (or suppressing activation of pro-inflammatory cells), angiogenic factors, and the like. Other means by which the support cells can accomplish their support function include having or displaying certain cell surface markers that attract or bind to other cell types, such as anti-inflammatory cells including but not limited to anti-inflammatory lymphocytes. Still other means by which the support cells can provide their support function include, but are not limited to, having stem cell-like qualities, such as but not limited to proliferation, differentiation and the like.

In some embodiments, the support cells comprise amniotic epithelial cells (AECs). In some embodiments, the support cells comprise mesenchymal stem cells, induced pluripotent stem cells, embryonic stem cells, adipose stem cells, or other adult stem cells such as but not limited to epithelial stem cells, or mixtures thereof. The support cells may be harvested from the same individual as the target cells, or the support cells may be harvested from the same species as the target cells. In other embodiments, the support cells may not be from the same species as the target cells. The support cells may be from a mammal. In certain embodiments, the support cells may be from a dog, cat, mouse, rat, cow, horse, pig, or a human or non-human primate. In particular embodiments, the support cells may be harvested from the same species as the subject on which the methods are being performed, including but not limited to the same individual. In certain embodiments, the support cells comprise human AECs and the subject on which the methods are being performed is a human.

A second population of cells in the mixture may comprise a population of target cells. The target cells may be any type of cell that can provide a therapeutic benefit to the subject. In general, the target cells may be intended to restore function or augment function of a tissue or organ. For example, the target cells may be a population of beta islet cells, a population of cardiomyocytes, a population of intestinal epithelial cells, a population of hepatocytes, a population of glomerulocytes, a population of lung cells, or a population of acinar cells.

The population of target cells may be mixed with the population of support cells. In some embodiments, the population of support cells may comprise AECs and the population of target cells may comprise beta islet cells. In some embodiments, the population of target cells may be mixed with at least two different populations of support cells. For example, the two populations of support cells may comprise two populations of cells selected from AECs, mesenchymal stem cells, induced pluripotent stem cells, embryonic stem cells, adipose stem cells, and other adult stem cells such as but not limited to epithelial stem cells. In certain embodiments, the two populations of support cells may include a population of AECs and a population selected from the group consisting of mesenchymal stem cells, induced pluripotent stem cells, embryonic stem cells, adipose stem cells, and epithelial stem cells.

The methods of the present invention include scenarios where the support cells may be mixed with the target cells prior to insertion into the sealed space. The present invention also includes scenarios where the target cells and support cells may be inserted separately into the sealed space and the mixing of the target cells and support cells occurs within the sealed space when the target cells and support cells come into contact with one another in the sealed space. In such embodiments, where the mixing occurs in the sealed space, the target cells may be inserted before or after the support cells. In certain embodiments the support cells may be inserted into the sealed space prior to the insertion of the target cells into the sealed space. In certain embodiments, the support cells may be inserted into the sealed space after the insertion of the target cells into the sealed space.

Standard cell culture techniques may be used to prepare the populations of cells in vitro. Both support cells and target cells may generally be cultured using routine cell culture techniques that are normal or accepted for the cell type being cultured. In some embodiments, the target cells and support cells may be human cells and may be cultured using animal-free (other than human) techniques and compositions. For example, when the target and/or support cells are human cells, the cells may be cultured in serum free conditions or the cells may be cultured using human serum rather than bovine serum.

Once adequate numbers of cells are generated in culture, the cells may then be harvested using standard techniques and placed in a liquid medium. Cells may be placed in any medium or buffer that is appropriate for a given cell type. For example, cells may be harvested from their in vitro environment and placed in buffer or other liquid medium, e.g., Hank's Balanced Salt Solution (HBSS), just prior to mixing with other cells or insertion into the space. Once harvested from the in vitro environment and placed in the appropriate liquid medium or buffer, the target cells and the support cells may be mixed simply by combining the harvested populations. In the alternative, each population of cells may be harvested from its in vitro environment and placed in the appropriate liquid medium or buffer and inserted separately into the sealed space, with mixing occurring within the sealed space.

The insertion of the populations of cells, either pre-mixed or not, may occur via any means that does not permanently disrupt the seal between the acellular membrane and the surface of the visceral organ. Such techniques for insertion include, but are not limited to, injection into the space using a syringe or insertion using a small pipette tip. The insertion of the cells may be done in a manner that is intended to lyse or destroy as few cells as possible during the insertion process. Accordingly, syringe needles should be chosen to accommodate the cells' passage into the sealed space without lysing the cells.

The population of cells for the support and target cells may each be homogenous or substantially homogenous populations of each cell type prior to mixing. The methods may include any number of cells for each of the support and target cells. For example, the population of support cells included in the mixture may be between about 100 and 1000 cells, between about $1 \times 10^3$ and $1 \times 10^4$ cells, between about $1 \times 10^4$ and $1 \times 10^5$ cells, between about $1 \times 10^5$ and $1 \times 10^6$ cells, between about $1 \times 10^6$ and $1 \times 10^7$ cells, between about $1 \times 10^7$ and $1 \times 10^8$ cells, between about $1 \times 10^8$ and $1 \times 10^9$ cells, or about $1 \times 10^9$ or more cells. Similarly, the population of target cells included in the mixture may be between about 100 and 1000 cells, between about $1 \times 10^3$ and $1 \times 10^4$ cells, between about $1 \times 10^4$ and $1 \times 10^5$ cells, between about $1 \times 10^5$ and $1 \times 10^6$ cells, between about $1 \times 10^6$ and $1 \times 10^7$ cells, between about $1 \times 10^7$ and $1 \times 10^8$ cells, between about $1 \times 10^8$ and $1 \times 10^9$ cells, or about $1 \times 10^9$ or more cells.

In some embodiments, if the target cells comprise beta islet cells, the beta islet cells may be intended to increase insulin production in an animal in which insulin production is lower than normal, including having no insulin production. To that end, the present invention also relates to methods of increasing glucose tolerance in a subject when the target cells comprise beta islet cells. In some embodiments, the methods of increasing glucose tolerance in a subject may be performed on a subject that has been diagnosed as a diabetic or pre-diabetic. In certain embodiments, the methods of increasing glucose tolerance in a subject may be performed on a subject that has been diagnosed as a type 1 diabetic. In certain embodiments, the methods of increasing glucose tolerance in a subject may be performed on a subject that has been diagnosed as a type 2 diabetic.

The methods may be accomplished using any surgical means, including but not limited to laparoscopic surgery and open surgery, provided that the surface of the visceral organ or tissue is accessible for placement of the acellular membrane.

The present invention may also relate to compositions comprising the outer surface of an intact visceral organ, an acellular membrane, and a mixture of a population of at least one type of support cell and at least one type of target cell. The composition may be configured to include a sealed space formed between the acellular membrane and the outer surface of the intact visceral organ, with the mixture of cells being disbursed in the sealed space.

EXAMPLES

The amniotic membrane was obtained from a placenta donated by a patient who received C-section surgery in the OB/GYN department of MedStar Georgetown University Hospital. Human AECs (hAECs) were isolated from one-quarter of the membrane, and the remaining three-quarters of the membrane were subjected to membrane preparation.

The hAECs were isolated using a modified version of a previously published method. See Gramignoli, R., et al., *Curr. Protoc. Stem Cell Biol.*, 37:1E.10.1-1E10-13 (2016) (doi: 10.1002/cpsc.2), published in Wiley Online Library. In particular, amniotic membrane was peeled off from placenta post-ethylene glycol tetraacetic acid (EGTA) rinsing. The harvested membrane was washed with calcium-free HBSS and digested with 0.05% Trypsin in a 37° C. water bath for 40 min. The hAECs were collected by centrifugation of the digest at 200 g×10 min at 4° C. after the first digestion. The membrane was then subjected to a second digestion by repeating the same procedure as for the first digestion. The hAECs were recovered by 200 g×10 min (4° C.) of centrifugation after the second digestion. All hAECs from each digestion were recombined into one conical tube at the last step.

SCID (Beige) mice, which possess both autosomal recessive mutations SCID (Prkdcscid) and beige (Lystbg), were purchased from the Charles River Laboratories, MD, and were used as human islet recipients. The study followed local guidelines at Georgetown University (GU), and was performed inside the GU animal facility under the approved IACUC protocol number 15-030. The SCID mice were rendered diabetic chemically by i.p. injection of 150 mg/kg Streptozotocin (STZ, Zanosar, GU hospital) in citrate buffer saline. Mice whose non-fasting blood glucose was over 250 mg/dL on two consecutive measurements were considered diabetic. The blood glucose levels were measured in the blood samples taken from the tail vein using a Bayor glucometer.

For the surgery on each mouse, under continuous 1-2% isoflurane anesthesia, a midline incision was made on the ventral abdominal wall, and the peritoneal cavity was open and the liver surface was exposed. A decellularized human amniotic membrane, 1.0×1.0 cm in size, was pasted on the diaphragm side of the left lobe liver surface (see FIG. 2A). 2000 islet equivalent (IEQ) of human islets was mixed with $4.0 \times 10^5$ hAECs in 100 µl of HBSS solution. The mixture of cells was infused into the space between the membrane and liver surface using a sterile 200 µl pipette tip. The incision was closed with 5-0 absorbable suture.

Figure 1B:
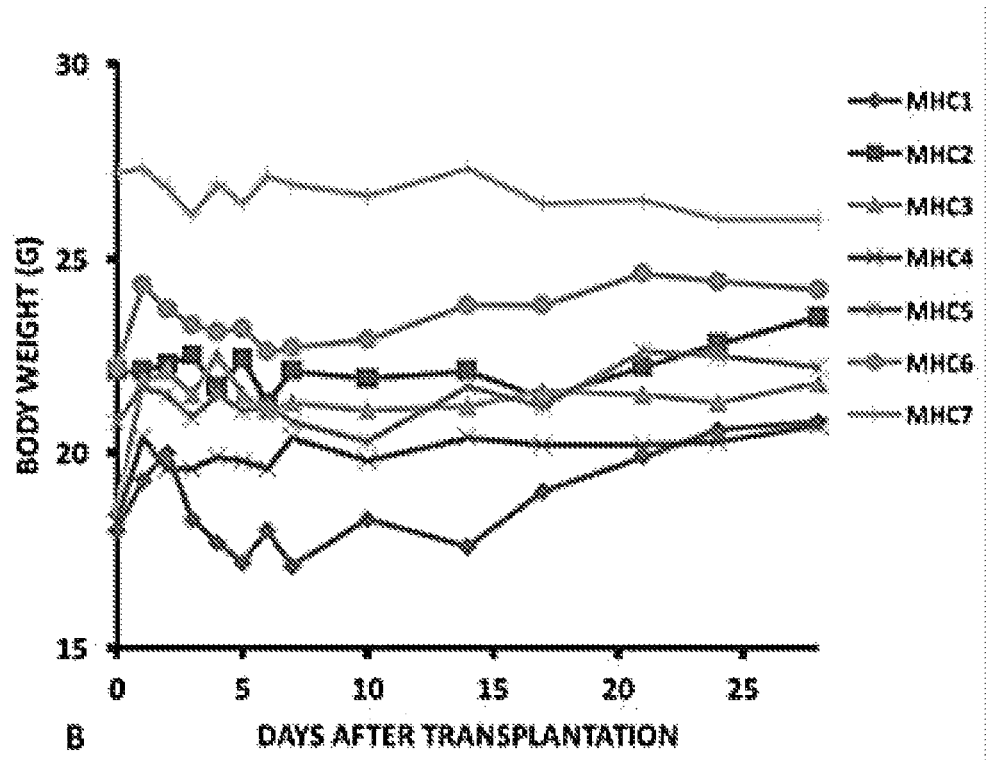

Mice undergoing islet transplantation were monitored by measuring non-fasting blood glucose daily for two weeks using a Bayor glucose monitor. Euglycemia was defined as non-fasting blood glucose less than 200 mg/dL on two consecutive days. As shown in FIG. 1A, all seven STZ-induced diabetic mice had a normal glucose level after transplantation. In addition, the body weight of each animal gradually increased post-transplantation (see FIG. 1B). Islet graft was confirmed as intact via histological examination 28 days after transplantation (FIG. 2B).

Figure 3A:
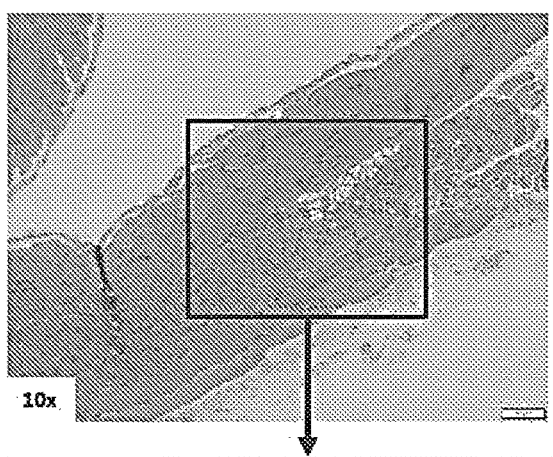
FIGS. 3A-3D show histological examination images that depict angiogenesis of the amniotic membrane harvested at 28 days both without hAECs embedded at the site of the mouse abdominal wall (FIGS. 3A and 3B) and with hAECs embedded at the site of the mouse abdominal wall (FIGS. 3C and 3D).
Figure 3B:
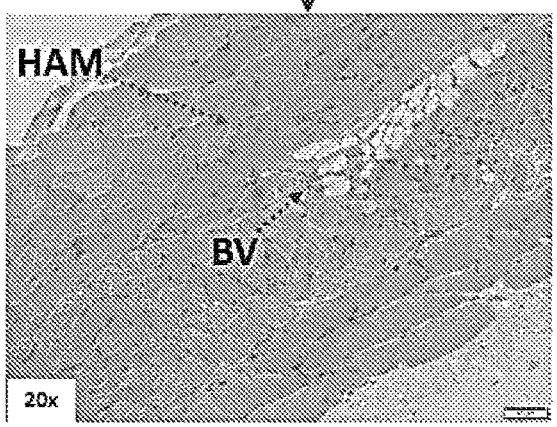
Figure 3C:
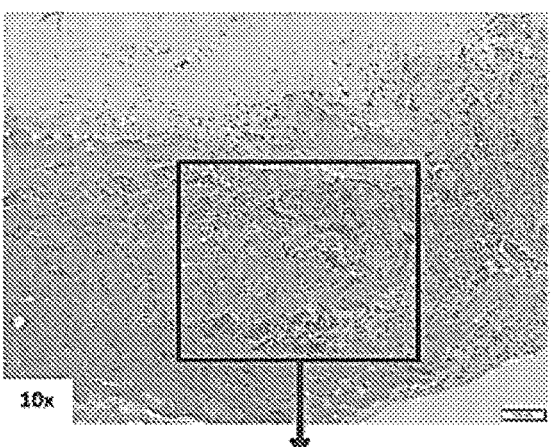
Figure 3D:
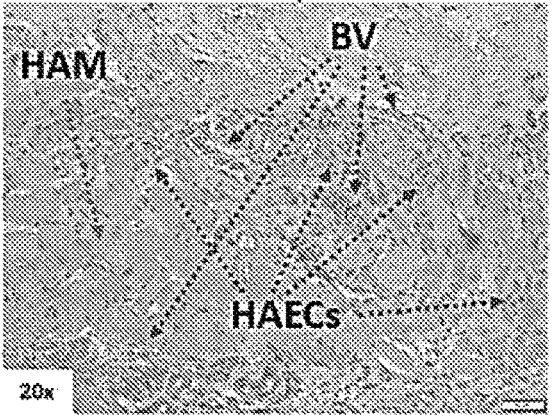

A comparison was made between mice that were delivered a mixture of cells without hAECs and mice that were delivered a mixture of cells with hAECs. FIGS. 3A and 3B show negligible angiogenesis in the amniotic membrane group without hAECs, whereas FIGS. 3C and 3D show facilitated and sustained angiogenesis, blood vessel formation, in the amniotic membrane group with hAECs.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of transplanting target cells into a subject in need thereof, the method comprising
   a) creating a sealed transplantation space by attaching an acellular membrane to the surface of a visceral organ in the subject in a manner such that a sealed space is created between the surface of the visceral organ and the membrane, and
   b) inserting a mixture of support cells and the target cells into the sealed transplantation space.

2. The method of claim 1, wherein the support cells are selected from the group consisting of amniotic epithelial cells, mesenchymal stem cells, epithelial stem cells, and a combination thereof.

3. The method of claim 1, wherein the target cells are selected from the group consisting of beta islet cells, cardiomyocytes, intestinal epithelial cells, hepatocytes, glomerulocytes, lung cells, acinar cells, and a combination thereof.

4. The method of claim 1, wherein the visceral organ is selected from the group consisting of liver, pancreas, kidney, small intestine, large intestine, stomach, ovaries, bladder, and lung.

5. The method of claim 1, wherein the acellular membrane is attached to the surface of a liver with an adhesive gel.

6. The method of claim 1, wherein the acellular membrane is attached to the surface of a liver without an adhesive gel.

7. The method of claim 1, wherein the acellular membrane comprises a decellularized amniotic membrane.

8. The method of claim 1, wherein the subject is diabetic or pre-diabetic.

9. A method of increasing glucose tolerance in a subject in need thereof, the method comprising
   a) creating a sealed transplantation space by attaching an acellular membrane to the surface of a visceral organ in the subject in a manner such that a sealed space is created between the surface of the visceral organ and the membrane, and
   b) inserting a mixture of support cells and the target cells into the sealed transplantation space;
   wherein the target cells comprise beta islet cells.

10. The method of claim 9, wherein the support cells are selected from the group consisting of amniotic epithelial cells, mesenchymal stem cells, epithelial stem cells, and a combination thereof.

11. The method of claim 9, wherein the visceral organ is the liver.

12. The method of claim 11, wherein the acellular membrane is attached to the surface of the liver with an adhesive gel.

13. The method of claim 9, wherein the acellular membrane comprises a decellularized amniotic membrane.

14. The method of claim 9, wherein the subject is diabetic or pre-diabetic.

* * * * *